US009765858B2

(12) United States Patent
Kelly (10) Patent No.: US 9,765,858 B2
(45) Date of Patent: Sep. 19, 2017

(54) EXPANDABLE GEAR SYSTEM AND METHODS FOR USE

(71) Applicant: SANFORD HEALTH, Sioux Falls, SD (US)

(72) Inventor: Patrick W. Kelly, Sioux Falls, SD (US)

(73) Assignee: Sanford Health, Sioux Falls, SD (US)

(*) Notice: Subject to any disclaimer, the term of this patent is extended or adjusted under 35 U.S.C. 154(b) by 187 days.

(21) Appl. No.: 14/471,717

(22) Filed: Aug. 28, 2014

(65) Prior Publication Data

US 2015/0065280 A1     Mar. 5, 2015

Related U.S. Application Data

(60) Provisional application No. 61/870,939, filed on Aug. 28, 2013.

(51) Int. Cl.
| | | |
|---|---|---|
| F16H 55/00 | (2006.01) | |
| F16H 59/00 | (2006.01) | |
| F16H 61/00 | (2006.01) | |
| F16H 63/00 | (2006.01) | |
| F16H 9/10 | (2006.01) | |
| F16H 55/54 | (2006.01) | |
| A61F 2/966 | (2013.01) | |
| A61F 2/95 | (2013.01) | |
| A61F 2/24 | (2006.01) | |
| A61F 2/82 | (2013.01) | |

(52) U.S. Cl.
CPC ............. *F16H 9/10* (2013.01); *A61F 2/966* (2013.01); *F16H 55/54* (2013.01); *A61F 2/24* (2013.01); *A61F 2/82* (2013.01); *A61F 2002/9517* (2013.01)

(58) Field of Classification Search
CPC ............. F16H 55/54; F16H 9/10; F16H 55/24; B62M 9/08; B62M 9/16
USPC ................................................. 474/47, 54, 49
See application file for complete search history.

(56) References Cited

U.S. PATENT DOCUMENTS

| 547,378 | A | * | 10/1895 | Gleason | ................. F16H 55/54 |
| | | | | | 474/54 |
| 652,763 | A | * | 7/1900 | Farnham | ................. F16H 55/54 |
| | | | | | 474/54 |
| 693,545 | A | * | 2/1902 | Jacobsen | ................. F16H 55/54 |
| | | | | | 474/53 |

(Continued)

FOREIGN PATENT DOCUMENTS

| DE | 10 2010 019045 | 11/2011 |
| GB | 757405 | 9/1956 |

OTHER PUBLICATIONS

International Search Report and Written Opinion for PCT/US2014/053149 dated Nov. 19, 2014.

*Primary Examiner* — Henry Liu
(74) *Attorney, Agent, or Firm* — McDonnell Boehnen Hulbert & Berghoff LLP (57) ABSTRACT

Example gear systems and methods for use are provided herein. An example gear system may include (a) an expandable gear that defines a plurality of circular sectors, (b) a hub disposed in the gear, where the hub includes an expandable portion, and (c) an expander, where the expandable gear has an expanded position when the expander is disposed within the hub and the expandable gear has an unexpanded position when the expander is disposed outside of the hub.

32 Claims, 9 Drawing Sheets

(56) References Cited

U.S. PATENT DOCUMENTS

| | | | | |
|---|---|---|---|---|
| 872,282 A * | 11/1907 | Geb | F16H 55/54 | 474/54 |
| 896,267 A * | 8/1908 | Benjamin | F16H 55/54 | 474/54 |
| 1,198,451 A * | 9/1916 | Jaurez | F16H 55/54 | 474/54 |
| 1,244,383 A * | 10/1917 | Snider | F16H 55/54 | 198/835 |
| 1,379,504 A * | 5/1921 | Young | F16H 9/10 | 474/53 |
| 1,545,658 A * | 7/1925 | Howe | F16H 55/54 | 474/54 |
| 1,626,240 A * | 4/1927 | Kosken | F16H 55/24 | 474/131 |
| 1,627,729 A * | 5/1927 | Dingee | B65H 75/242 | 242/573.6 |
| 1,674,635 A * | 6/1928 | Burden | B41F 27/105 | 101/375 |
| 1,838,104 A * | 12/1931 | Meglitz | F16H 55/54 | 474/54 |
| 1,875,385 A * | 9/1932 | Maas | F16H 55/54 | 474/54 |
| 1,943,435 A * | 1/1934 | Hertenstein | F16H 55/54 | 474/54 |
| 1,963,816 A * | 6/1934 | Whitten | F16H 55/54 | 474/54 |
| 2,022,115 A * | 11/1935 | Howe | F16H 9/22 | 474/54 |
| 2,266,538 A * | 12/1941 | Evans | D05B 35/06 | 112/152 |
| 2,341,273 A * | 2/1944 | Helberg | B64C 13/30 | 474/109 |
| 2,555,570 A * | 6/1951 | Carter | D21F 7/02 | 474/54 |
| 4,478,594 A * | 10/1984 | Gayer | F16H 7/08 | 474/13 |
| 4,498,351 A * | 2/1985 | Ahoor | F16H 9/10 | 474/54 |
| 4,516,960 A * | 5/1985 | Rathert | F16H 55/54 | 474/47 |
| 4,530,676 A * | 7/1985 | Leonard | F16H 9/10 | 474/49 |
| 4,810,236 A * | 3/1989 | Kumm | F16H 9/10 | 474/101 |
| 4,946,426 A * | 8/1990 | Leonard | B62M 9/08 | 474/101 |
| 4,969,857 A * | 11/1990 | Kumm | F16H 61/6624 | 474/49 |
| 5,006,094 A * | 4/1991 | Leonard | B62M 9/08 | 474/101 |
| 5,013,284 A * | 5/1991 | Leonard | F16H 55/54 | 280/214 |
| 5,492,506 A * | 2/1996 | Lorance | F16H 55/54 | 474/49 |
| 5,582,555 A * | 12/1996 | Miller | F16H 55/54 | 474/148 |
| 8,932,161 B2 * | 1/2015 | Easterday, III | F16H 55/54 | 474/47 |
| 2007/0054766 A1* | 3/2007 | Shamis | F16H 55/54 | 474/47 |
| 2012/0172963 A1 | 7/2012 | Ryan | | |
| 2013/0065717 A1* | 3/2013 | Easterday, III | F16H 55/54 | 474/50 |

* cited by examiner

EXPANDABLE GEAR SYSTEM AND METHODS FOR USE

CROSS-REFERENCE TO RELATED APPLICATION

This application claims the benefit of the filing date of U.S. Provisional Patent Application Ser. No. 61/870,939, filed Aug. 28, 2013, entitled "Expandable Gear System and Methods for Use," which is hereby incorporated by reference in its entirety.

BACKGROUND

Unless otherwise indicated herein, the materials described in this section are not prior art to the claims in this application and are not admitted to be prior art by inclusion in this section.

Stent deployment devices are utilized to direct the placement of a stent in a human or animal body and to ultimately eject and deploy a stent in a targeted lumen. Typically, when a stent is in a constrained and compressed condition, the stent has a length that is much longer than when the stent is in an unconstrained and expanded condition. Some stent deployment devices have been developed to push the device while simultaneously retracting the sheath with a goal of maintaining a distal end of the stent at a targeted location upon deployment from the sheath. These customary methods and devices typically deploy stents in a manner that moves the stent in a back-and-forth motion. This may result in the stent structure making delayed contact with the target lumen's wall and the stents becoming elongated in vivo.

SUMMARY

The present invention provides an expandable gear system and methods for a stent deployment device and methods of use thereof that may beneficially permit a user to shorten the expanded length of a stent or stent graft upon deployment. Specifically, an expandable gear may be in mechanical communication with an apparatus that either retracts a sheath or that advances a stent or stent graft. This expandable gear may have a neutral unexpanded position and that may be transitioned to an expanded position thereby increasing the gear's diameter and effectively altering the rate of retraction of the stent sheath or the rate of advancement of the stent graft.

Adjusting the rate of deployment of a stent graft may be valuable by providing a user with more control over the degree to which the stent is "packed" in a vessel or lumen. For instance, if the diameter of the expandable gear is modified to increase the rate of stent advancement or to decrease the rate of sheath retraction, then the stent will be slightly shorter than its original unconstrained length. A shorter deployed stent may advantageously increase the radial strength and resistance of the stent in a heavily calcified resilient stenosis in an artery, for example. Alternatively, the expandable gear may be coupled to the sheath retraction apparatus and the diameter of the expandable gear may be increased to "depack" and elongate the stent. This may have the advantage of providing additional control in regions where the vessel lumen is smaller or where the stent needs to be slightly elongated. The expandable gear system and methods may also beneficially result in more accurate stent placement in a targeted zone.

Thus, in one aspect, a gear system is provided including the features of: (a) an expandable gear that defines a plurality of circular sectors, (b) a hub disposed in the gear, where the hub includes an expandable portion, and (c) an expander, where the expandable gear has an expanded position when the expander is disposed within the hub and the expandable gear has an unexpanded position when the expander is disposed outside of the hub.

In a second aspect, a method for using the expandable gear system is provided including the steps of (a) applying a force to a push-button of the gear system according to the first aspect and (b) advancing an expander into a hub of an expandable gear, thereby increasing a diameter of the gear.

These as well as other aspects, advantages, and alternatives, will become apparent to those of ordinary skill in the art by reading the following detailed description, with reference where appropriate to the accompanying drawings.

DETAILED DESCRIPTION

Example expandable gear systems, as well as methods of use, are described herein. Any example embodiment or feature described herein is not necessarily to be construed as preferred or advantageous over other embodiments or features. The example embodiments described herein are not meant to be limiting. It will be readily understood that certain aspects of the disclosed methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, with respect to measurements and calculations, "about" means+/−10%.

As used herein, "adjoined" means close to or in contact with.

As used herein, a "circular sector" refers to a portion of a gear that is defined by two gear radii and an arc at the gear's perimeter. As such, a circular sector is generally wedge-shaped. The circular sector has a central angle disposed between the two gear radii. In some embodiments, the portion of the circular sector disposed at the center of the gear may be removed to accommodate a hub or axle.

As used herein, "stent" is used broadly to refer to both stents and stent grafts, and "stent graft" is likewise broadly used to refer to both stents and stent grafts. The stent or stent graft may be self-expandable. As used herein, a "stent" is typically a cylindrical frame and means any device or structure that adds rigidity, expansion force, or support to a prosthesis or native vasculature, while a "stent graft" refers to a prosthesis comprising a stent and a graft material associated therewith that forms a lumen through at least a portion of its length. The graft material may permit blood perfusion in some embodiments. For example, the stent structure may comprise coiled, mesh, zig zag, braided, knitted or woven wires. The stent structure could also comprise a laser cut sheet or a laser cut tube that may have various lengths, diameters or wall thickness. Alternatively, the stent may comprise injection molded metal. A "graft" is a cylindrical liner that may be disposed on the stent's interior, exterior or both. Further, when used in combination with a graft, the stent structure may further comprise a series of spaced apart stent rings disposed along the graft. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality nitinol, cobalt chromium, stainless steel wires, nickel and titanium alloys, and biocompatible plastics attached to a graft. Any suitable graft material can be used. In various embodiments, the graft material is a biocompatible fabric, including but not limited to woven or knitted polyester, such as poly(ethylene terephthalate), polylactide, polyglycolide and copolymers thereof; fluorinated polymers, such as PTFE, including extruded, electrospun or expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

The covered stent grafts can be made of any suitable material, including but not limited to polytetrafluoroethylene (ePTFE) lined nickel-titanium alloy stent. The stent grafts are preferably covered and flexible. The stent grafts may contain any other suitable components, such as surface modifications including but not limited to covalent attachment of heparin.

A stent may have an unconstrained, expanded length $L_u$ and a constrained, compressed length $L_c$. The unconstrained length $L_u$ of the stent or stent graft may range from about 40 mm to about 200 mm and, in various embodiments, may be between about 40-180 mm, 40-160 mm, 40-140 mm, 40-120 mm, 40-100 mm, 40-80 mm, 40-60 mm, 60-200 mm, 80-200 mm, 100-200 mm, 120-200 mm, 140-200 mm, 160-200 mm, 180-200 mm, 40 mm, 60 mm, 80 mm, 120 mm or 200 mm. The constrained length $L_c$ of the stent is a factor of the stent's unconstrained diameter, the length of the unconstrained stent, the weave pattern of a woven stent and the size of the French sheath into which the stent is to be constrained.

In various embodiments, a first gear may be coupled to a push apparatus, such as a shaft for advancing the stent, and the second gear may be coupled to a pull apparatus, such as a sheath for retraction. In various embodiments, the first gear, the second gear or both the first and second gear may be expandable. Example push and pull apparatus are disclosed in U.S. patent application Ser. Nos. 13/943,863 and 13/974,626. In example embodiments in which only the first gear is expandable, if a driving mechanism, like a thumbwheel or a motor, is operating at a constant speed and is coupled to the axle of the first gear, then the velocity of a driving belt coupled to the first gear will increase as the first gear expands and the angular velocity of the second gear will increase, effectively increasing the rate at which the push or pull apparatus coupled to the second gear advances or retracts, respectively. If instead the driving mechanism is coupled to the axle of the non-expandable second gear, the angular velocity of the first gear will decrease as the first gear expands and the rate at which the push or pull apparatus coupled to the first gear advances or retracts, respectively, will also decrease. In addition, if the driving mechanism is instead coupled to the driving belt, the angular velocity of the first gear will decrease as the first gear expands and the rate at which the push or pull apparatus coupled to the first gear advances or retracts, respectively, will also decrease, and the angular velocity of the second gear will effectively remain the same.

In additional embodiments, the "stent" may also include septal, patent foramen ovale or percutaneous, transcatheter occluders or self-expanding valves, such as the Corevalve® manufactured by Medtronic, that each have a constrained and an unconstrained length.

Further, in various embodiments, it may be desirable to "pack" the stent into the vessel in which the stent is being deployed such that the deployed stent is 0-20% shorter than the original unconstrained length, for example. Stent "packing" may be desirable because it may cause the stent to apply additional radial force to the vessel. Stent "packing" may be achieved by modifying the ratio of the first gear diameter to the second gear diameter and thereby applying additional force to the apparatus advancing the stent. Specifically, in one embodiment, a ratio of the first gear diameter to the second gear diameter may be adjusted during deployment to be equal to the stent ratio plus 0-20% of the stent ratio, for example.

In addition, in an example embodiment in which both the first gear and the second gear are expandable and the driving mechanism is coupled to the driving belt, the first gear may be in its expanded position initially. If an operator desires to alter the packing of the stent, the operator may advance the first expander partially or completely out of the first gear while at the same time advancing the second expander into a hub of the second gear. In this embodiment, if the push apparatus is coupled to the first gear and the pull apparatus is coupled to the second gear, then the rate of advancement of the stent will increase as the expander retracts from the first gear and the rate of sheath retraction will decrease as the second expander moves into the hub of the second gear.

In one aspect, the invention provides a gear system, comprising:

an expandable gear that defines a plurality of circular sectors;

a hub disposed in the gear, wherein the hub comprises an expandable portion; and an expander, wherein the expandable gear has an expanded position when the expander is disposed within the hub and the expandable gear has an unexpanded position when the expander is disposed outside of the hub.

Figure 1A:
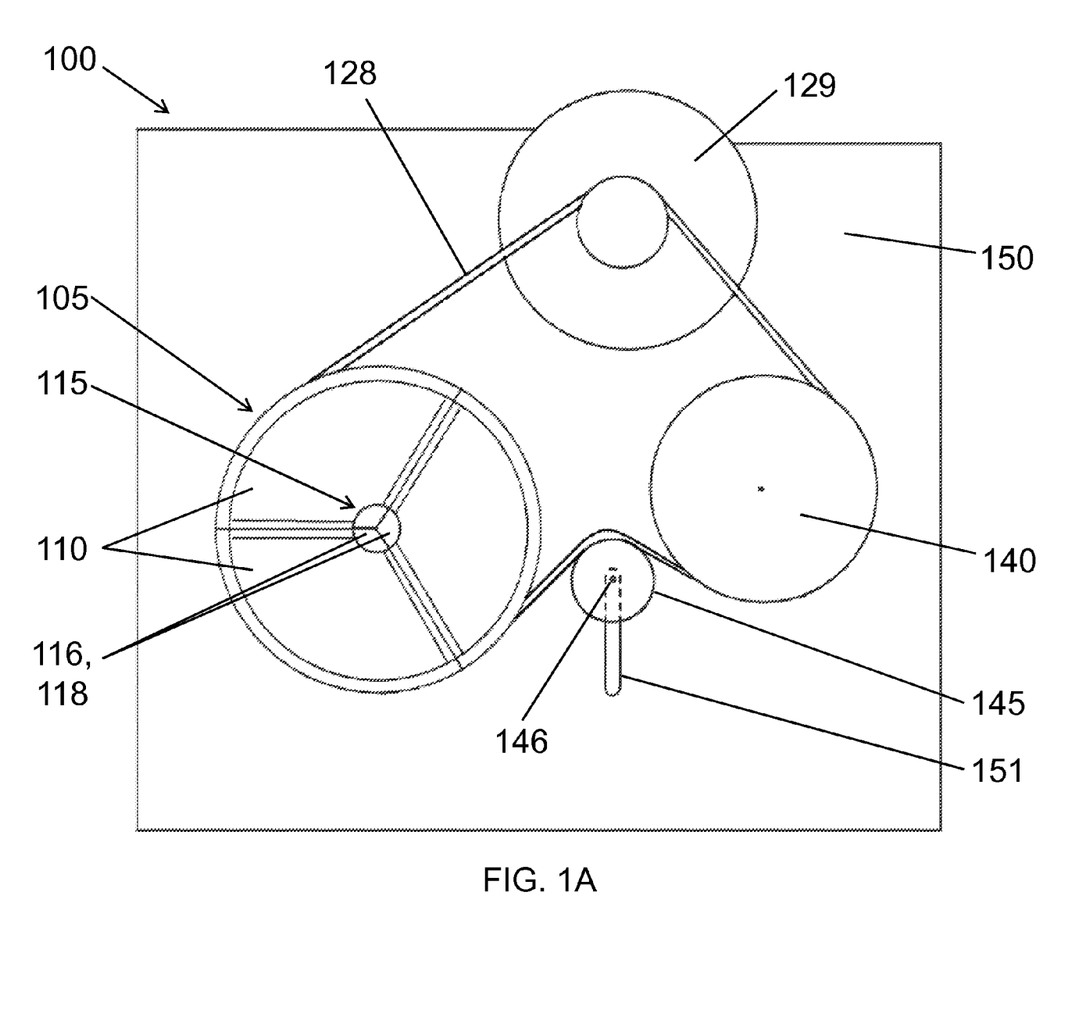
FIG. 1A shows a front view of a gear system in an unexpanded position according to one embodiment.

Referring now to FIGS. 1-4A, like numbers denote like features in FIGS. 1A-4B. A gear system 100 is shown in FIGS. 1A-1B including an expandable gear 105. As used herein, a "gear" is toothless and belt driven, similar to a pulley. The gear defines a plurality of circular sectors 110 that may have central angles that total 360 degrees. As shown in FIG. 1A, the expandable gear 105 has an unexpanded position in which the plurality of circular sectors 110 may be adjoined essentially forming a contiguous perimeter. As shown in FIG. 1B, the gear 105 also has an expanded position in which the plurality of circular sectors 110 may be displaced in a direction away from the center of the gear 105 effectively increasing the diameter of the gear 105. In one embodiment, shown in FIG. 2A, the gear 205 is in an expanded position and has three circular sectors 210 each having a central angle of about 120 degrees. In another embodiment, shown in FIG. 2B, the gear 205 is in an expanded position and has four circular sectors 210 each having a central angle of about 90 degrees. In various other embodiments, the plurality of circular sectors may be as few as two circular sectors. In various other embodiments, more than four circular sectors are contemplated.

In one embodiment, an expandable band 125 may be disposed about a circumference of the expandable gear 105. The band 125 may be configured to expand and contract when the gear 105 transitions between the unexpanded position and the expanded position. The band may be made of a stretchable material that may be repeatedly deformed and returned to its original shape, including, but not limited to, rubber. The band 125 may be configured to maintain a continuous surface about the gear's circumference for contact and frictional engagement with a driving belt 128, discussed in more detail below. In a further embodiment, shown in FIG. 4A, a groove 406 may be defined along the circumference of the expandable gear 405, and the expandable band 425 may include a rib 426 sized and shaped to mate with the groove 406 of the expandable gear 405.

Figure 1B:
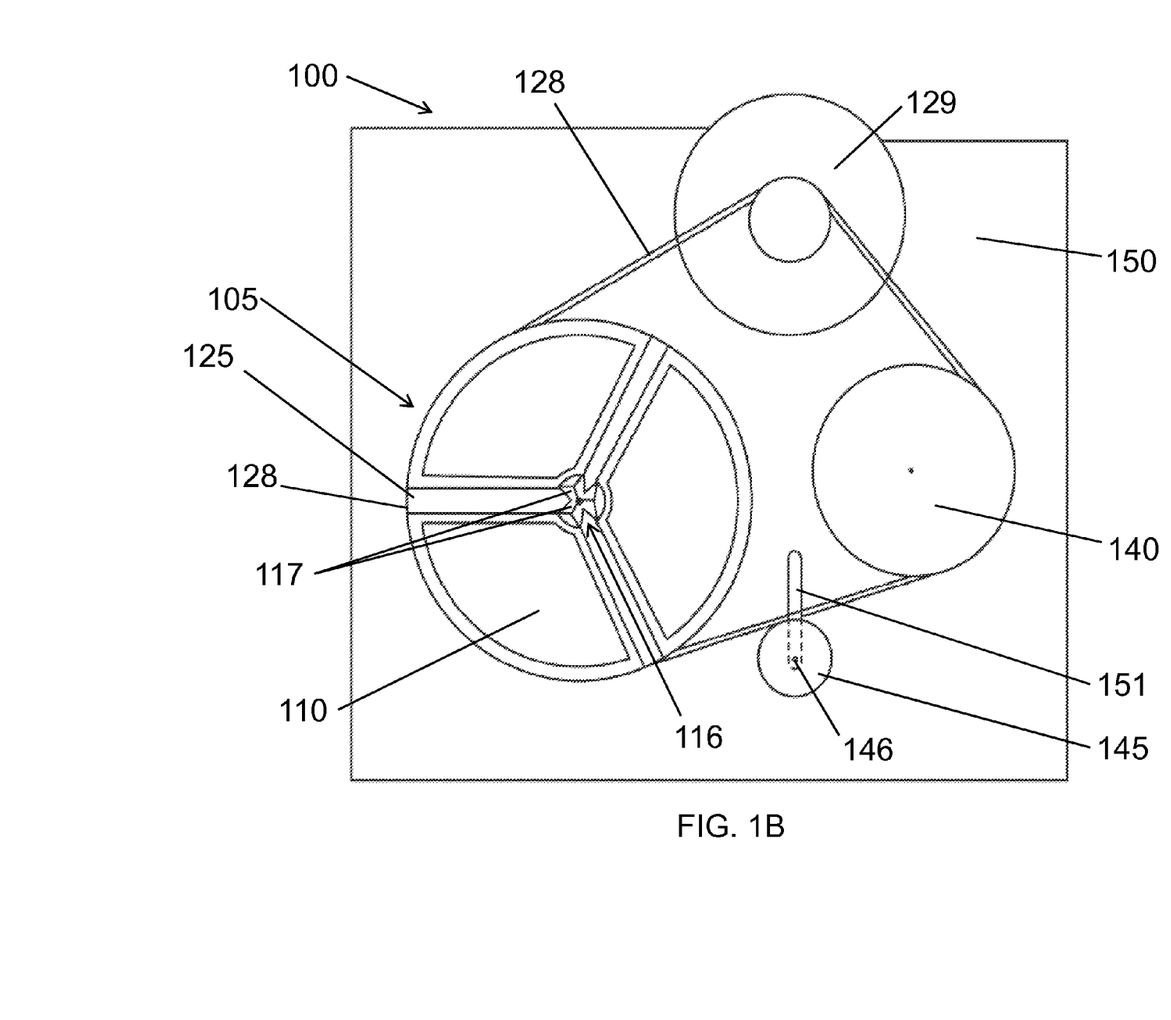
FIG. 1B shows a front view of a gear system in an expanded position according to the embodiment shown in FIG. 1A.
Figure 2A:
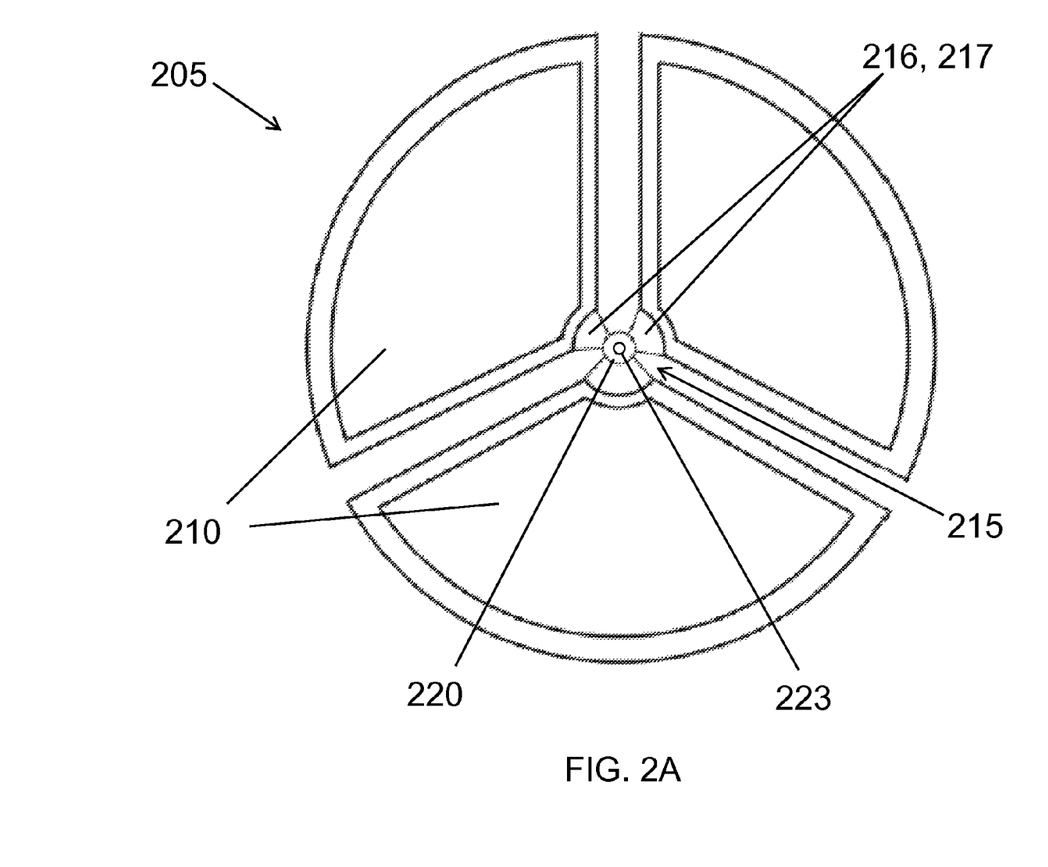
FIG. 2A is a front view of a gear, according to one embodiment, in an expanded position, the gear having three circular sectors each having a central angle of about 120 degrees.
Figure 2B:
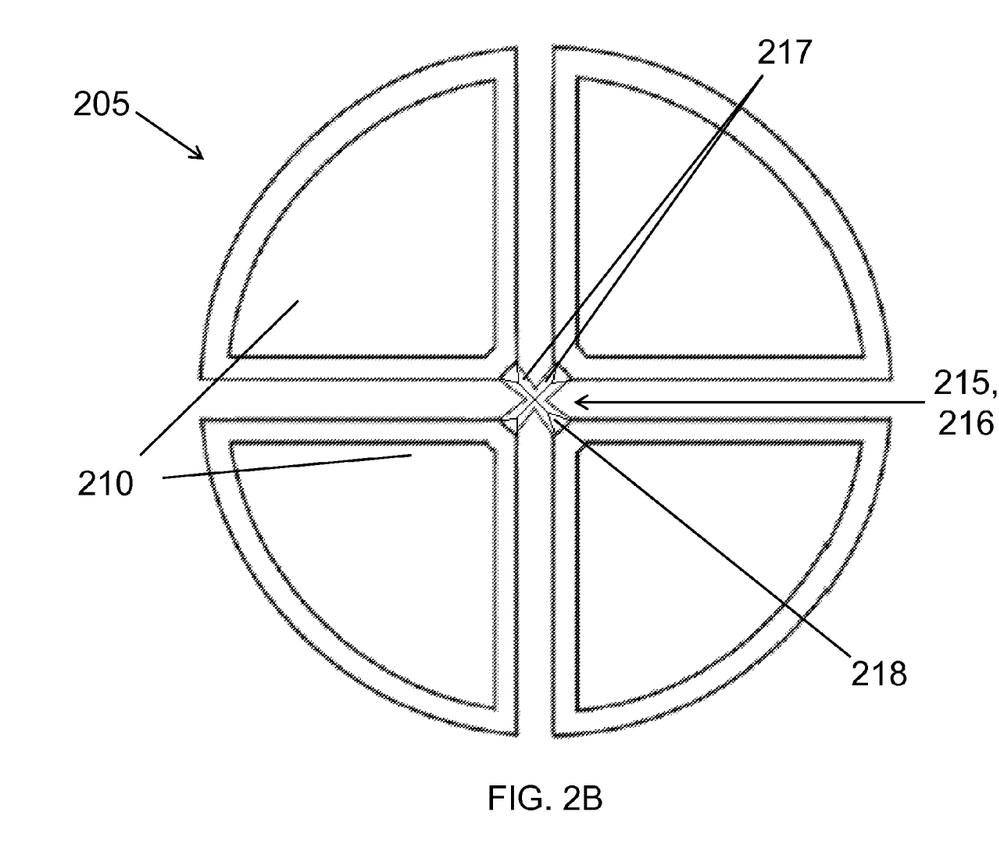
FIG. 2B is a front view of a gear, according to one embodiment, in an expanded position, the gear having four circular sectors each having a central angle of about 90 degrees.

In one embodiment, the gear system 100 may include a belt 128 in mechanical communication with the expandable gear 105. The belt 128 may be a loop of flexible material used to mechanically link two or more gears having shafts or axles capable of rotation. The belt may take the form of a "V" belt, flat belt, round belt, ribbed belt or multi-groove belt, among other possibilities. The belt 128 may transmit power generated by a motor or a thumb-wheel 129, for example, to one or more toothless gears 105, 140, 145 in the gear system 100 via frictional engagement.

For example, in one embodiment, the gear system 100 may comprise a single expandable gear 105 and a solid non-expandable gear 140. In one embodiment, the single expandable gear 105 may be smaller than the solid gear 140 in the unexpanded position, the same size as the non-expanded gear 140 when the expander has been partially advanced into the hub 115 in an intermediate expanded position and larger than the solid gear when the expander (see FIGS. 3A-4B) has been completely advanced into the hub 115 in a fully expanded position, for example. In one embodiment, in which all of the gears 105, 140 in the gear system are on axles fixed in place relative to a gear support 150, the belt 128 may be elastic such that the belt 128 is capable of expanding to account for any expansion in the expandable gear 105.

In another embodiment, the gear system 100 may include a stabilizing gear 145 in mechanical communication with the expandable gear 105 via the belt 128. In a further embodiment, an axle 146 may be coupled to the stabilizing gear 145 and the axle may be moveably disposed in a channel 151 defined in the gear support 150 such that the axle 146 of the stabilizing gear 145 may be repositioned within the channel 151 from a neutral position (FIG. 1A) to a tensioned position (FIG. 1B). In the neutral position of the stabilizing gear 145, the expandable gear 105 is in its unexpanded position, and, in the tensioned position of the stabilizing gear 145, the expandable gear 105 is in its expanded position. In this embodiment, the belt 128 may be substantially inelastic, meaning that rather than expanding to account for expansion of the expandable gear 105, the belt 128 instead acts upon the stabilizing gear 145 in response to gear expansion and causes the axle 146 of the stabilizing gear 145 to move out of the neutral position in the channel 151. In still another embodiment, a spring (not shown) may be in mechanical communication with the axle 146 of the stabilizing gear, biasing the stabilizing gear 145 toward the neutral position.

Figure 3A:
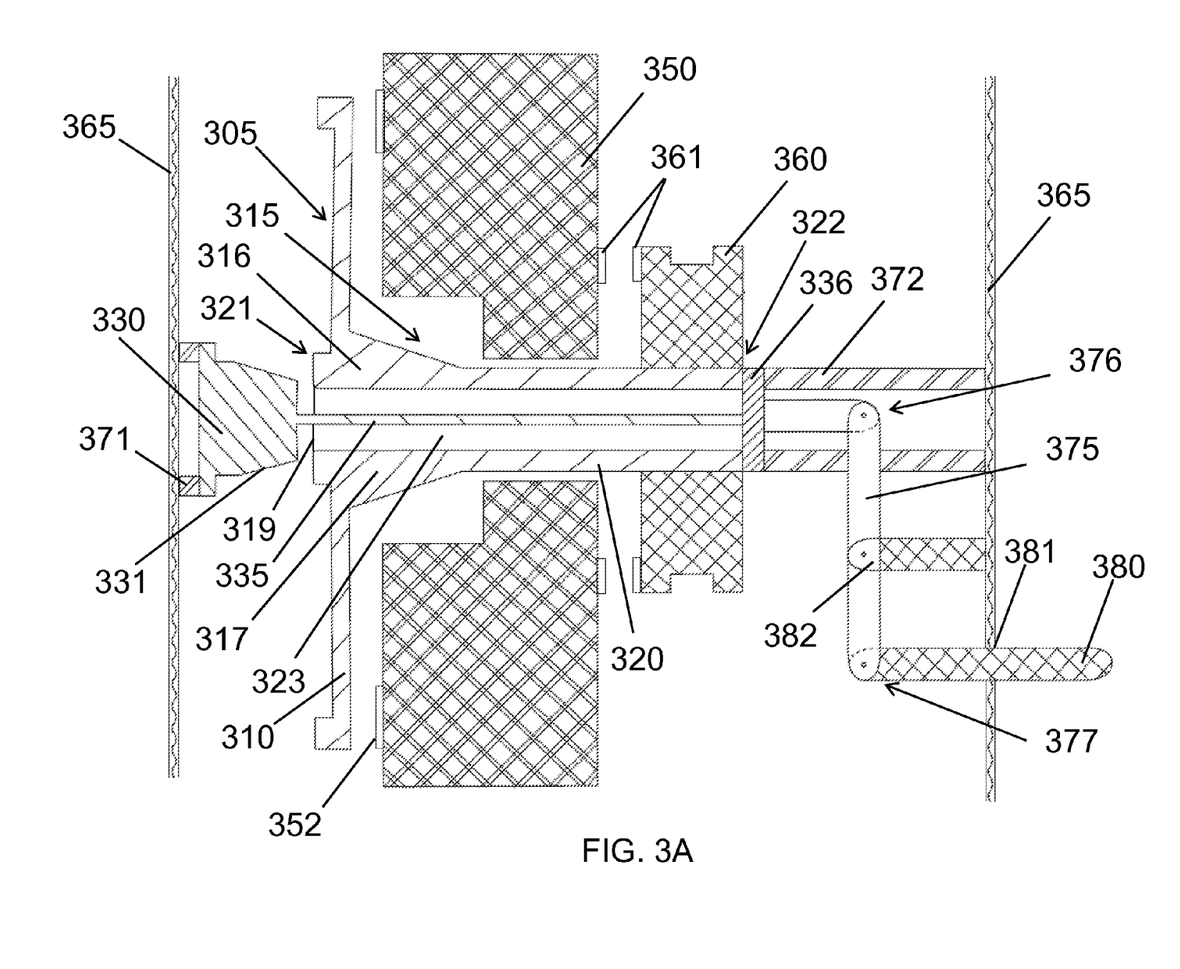
FIG. 3A is a top cross-sectional view of a gear and expander in an unexpanded position, according to one embodiment.
Figure 3B:
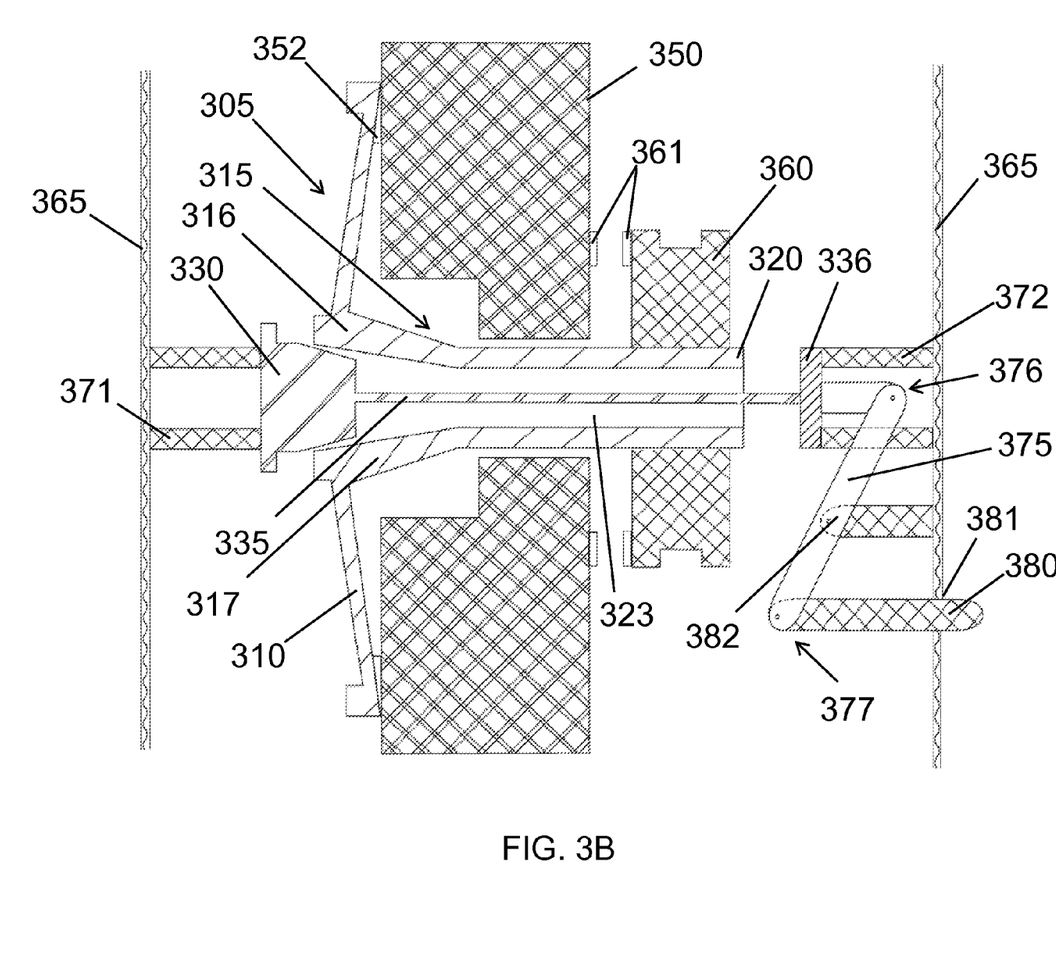
FIG. 3B is a top cross-sectional view of a gear and expander in an expanded position, according to the embodiment of FIG. 3A.
Figure 4A:
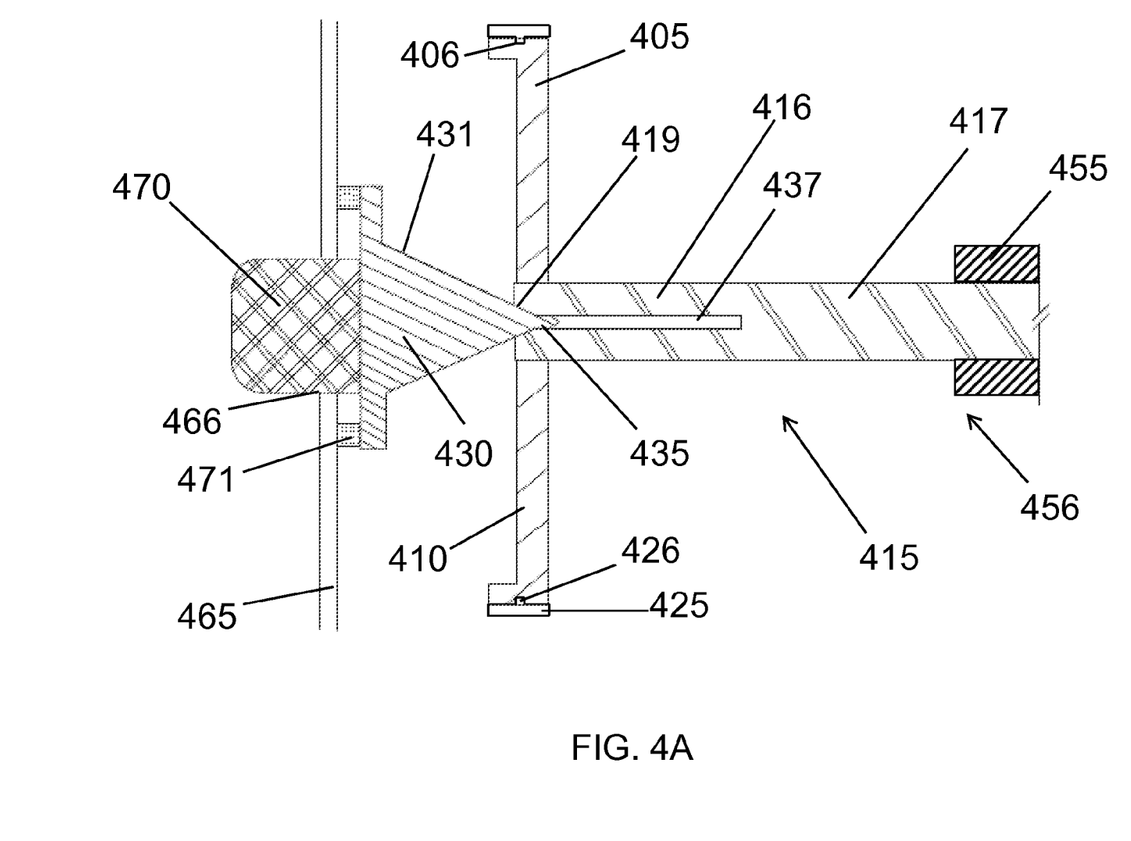
FIG. 4A is a top cross-sectional view of a gear and expander in an unexpanded position, according to one embodiment.
Figure 4B:
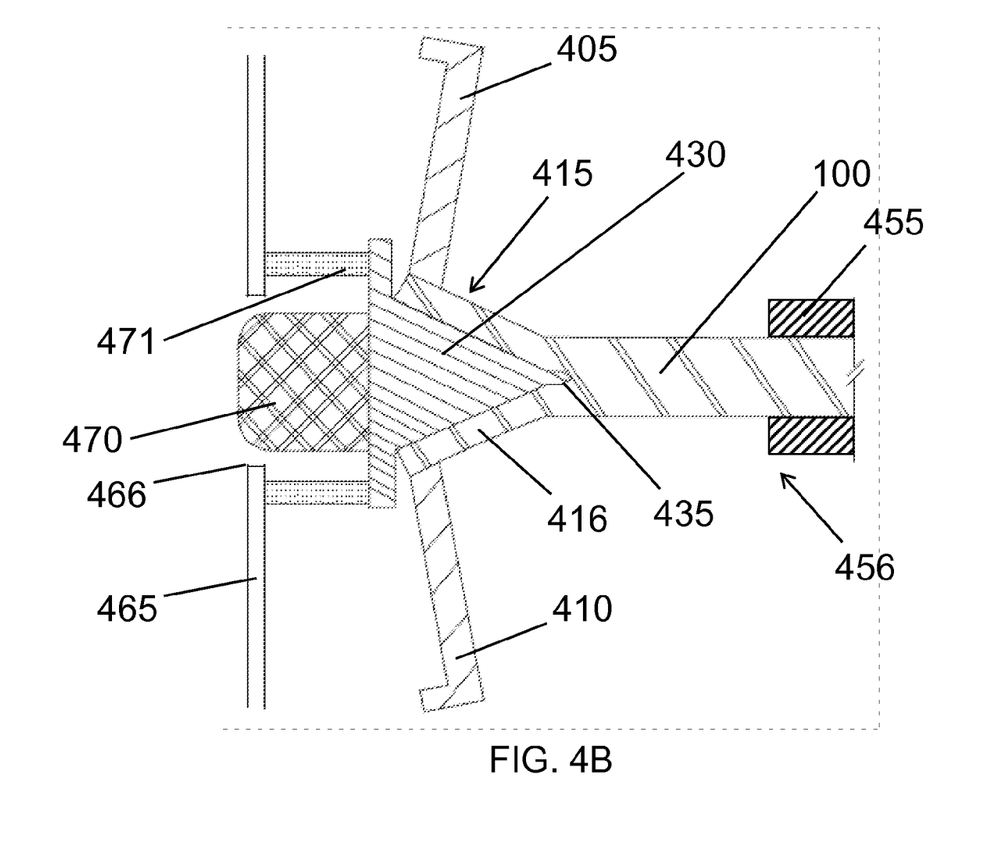
FIG. 4B is a top cross-sectional view of a gear and expander in an expanded position, according to the embodiment of FIG. 4A.

The expandable gear 105 includes a hub 115 disposed in the gear 105 and is preferably disposed in the center of the gear. The hub 115 includes an expandable portion 116 that may be displaced along with the plurality of circular sectors 110. In various embodiments, the hub 115 may be formed as a separate component or as a single unitary piece with the gear 105 via injection molding, for example. In one embodiment, the expandable portion 116 of the hub 115 may include a plurality of limbs 117. In a further embodiment, the expandable portion 116 of the hub 115 may have a cross-section defining a plurality of circular sectors 118 that correspond to the plurality of limbs 117 in the unexpanded position. In one embodiment, as shown in FIGS. 3A-B, the hub 315 may include an axle 320 having a first end 321 and a second end 322. The expandable portion 316 of the hub 315 may be defined at the first end 321 of the axle 320 and may be coupled to the expandable gear 305. The expandable portion 316 of the hub 315 may extend along the axle 320 towards the second end 322 of the axle 320. In an alternative embodiment, shown in FIGS. 4A-4B, the hub 415 may include a coupling 455 having a first end 456 and a second end (not shown). The first end 456 of the coupling 455 may be attached to a non-expandable portion 417 of the hub 415. In turn, the second end of the coupling 455 may be configured to attach to an axle (not shown). In one embodiment, the coupling 455 may include a hollow tube, as shown in FIGS. 4A-4B, that may be press-fit over, or otherwise attached to, the axle via known couplings and connectors. In an alternative embodiment, the coupling 455 may include a spline joint, among other possibilities.

The gear system 100 further includes an expander 330, 430, shown in FIGS. 3A-4B. In one embodiment, the expander 330, 430 may have a tapered outer surface 331, 431. For example, the expander 330 may have a frustum shape (FIGS. 3A-B) or a cone shape (FIGS. 4A-B), among other possibilities. As shown in FIGS. 3A and 4A, when the expander 330, 430 is disposed substantially outside of the hub 315, 415, the expandable gear 305, 405 has an unexpanded position in which the plurality of circular sectors 310, 410 may be adjoined essentially forming a contiguous perimeter. As shown in FIGS. 3B and 4B, when the expander 330, 430 is disposed within the hub 315, 415, the gear 105 has an expanded position in which the plurality of circular sectors 110 may be displaced in a direction away from the center of the gear 305, 405 effectively increasing the diameter of the gear 305, 405. The expanded position may include any intermediate angle of deflection up to and including a fully expanded angle of deflection that is achieved when the expander 335, 435 has completely advanced into the hub. In the fully expanded position, the plurality of circular sectors 310, 410 may be angled back toward the gear support 150 and interface with low friction pads 152 positioned on the gear support or on the back side of the expandable gear 305, 405 near the periphery of the gear 305, 405. In various embodiments, the expander 330, 430, the hub 315, 415 and/or the pads 152 may be made of a low-friction material, such as Delrin, to allow the gear 305, 405 to freely permit the gear 305, 405 to rotate about the expander 330, 430 during stent deployment.

In another embodiment, the plurality of circular sectors may taper in thickness such that the circular sectors are thicker at the circumference of the gear than relative to the thickness at the hub. This arrangement may permit the plurality of circular sectors to flex relative to the hub to remain substantially in the same plane as the wheel transitions between an unexpanded position and an expanded position.

In one embodiment, the expander 330, 430 may be coaxially aligned with the hub 315, 415 of the gear 305, 405. In another embodiment, the hub 315, 415 may define an opening 319, 419 in the unexpanded position, and the expander 330, 430 may include a guide stem 335, 435 at least partially disposed in the opening 319, 419 of the hub 315, 415. In operation, the guide stem 335, 435 may be used to maintain alignment between the expander 330, 430 and the gear 305, 405, when the gear 305, 405 is in an unexpanded position.

For example, in one embodiment shown in FIGS. 3A-3B, the expandable portion 316 of the hub 315 may be coupled to an axle 320 having a hollow core 323. In this embodiment, the guide stem 335 may extend through the expandable portion 316 of the hub 315 and through the hollow core 323 of the axle 320 in both the expanded and unexpanded positions. In a further embodiment, a flange 336 may be defined at the end of the guide stem 335 opposite to the expander 330.

Alternatively, in another embodiment shown in FIGS. 4A-4B, the guide stem 435 may be configured to extend into and advance along a channel 437 defined in the expandable portion 416 of the hub 415. In one embodiment, the plurality of limbs 417 of the hub 415 define the channel 437 in the unexpanded position. Then, as the expander 430 advances along the channel 437, the plurality of limbs 417 expand and separate to accommodate the expander 430 and thereby increase the effective diameter of the gear 405.

In one embodiment, the free end of axle 320 may be coupled to one of a push reel 360 or a pull reel the second end 322 of the axle 320. The push or pull reel 360 may in turn be coupled to a stent advancer or sheath. Low friction pads 361 may also be disposed between the gear box 350 and the push or pull reel 360.

In one embodiment, the gear system 100 may include a housing 365, 465. The housing 365, 465 may enclose the gear system 100 providing a protective cover. In one embodiment, the thumbwheel 129 may partially or wholly extend out of the housing 365, 465. In a further embodiment, a recoil material 371, 471 may be coupled between the housing 365, 465 and the expander 330, 430 such that the expander 330, 430 is biased toward the unexpanded position. In another embodiment, a recoil material 372 may be coupled between the housing 365 and a flange 336 coupled to the end of an elongated guide stem 335 such that the expander 330 is biased toward the unexpanded position.

In one embodiment, the gear system 100 may include a first push-button 470 coupled to the expander 430 and arranged on a surface of the expander 430 opposite to the guide stem 435. The first push-button 470 may be configured to receive a force from a user's finger or thumb and to advance the expander a given distance into the respective gear. In a further embodiment, a portion of the first push-button 470 may be disposed through a first opening 466 in the housing 465.

In another embodiment, the gear system 100 may include a lever arm 375 having a first end 376 and a second end 377. The first end 376 of the lever arm 375 may be coupled to the guide stem 335 and the second end 377 of the lever arm 375 is coupled to a second push-button 380. In a further embodiment, a portion of the second push-button 380 may be disposed through a second opening 381 in the housing 365. The lever arm 375 may be pivotally coupled to the housing 365 at a point 382 between the first and the second end 376, 377 of the lever arm 375.

In an alternative embodiment, two expandable gears may be employed. Two expanders may each may be aligned with a central axis of the expandable gears. A lever may be coupled at a first end to one expander and at a second end to the other expander. A fulcrum or pivot point may be coupled to the housing and to the lever at a point between the first and second ends. A first push-button may be arranged opposite the first expander and a second push-button may be arranged opposite the second expander. In one embodiment, the lever may be biased toward a neutral position by a recoil material on either side of the fulcrum or pivot point. In the neutral position, the two gears may have the same size and the expanders may be partially disposed within both respective hubs of the gears. As a force is applied to one of the push-buttons the corresponding expander advances further into the hub of the first gear and further out of the second gear. This increases the diameter of the first gear while decreasing the diameter of the second gear at the same time.

Figure 5:
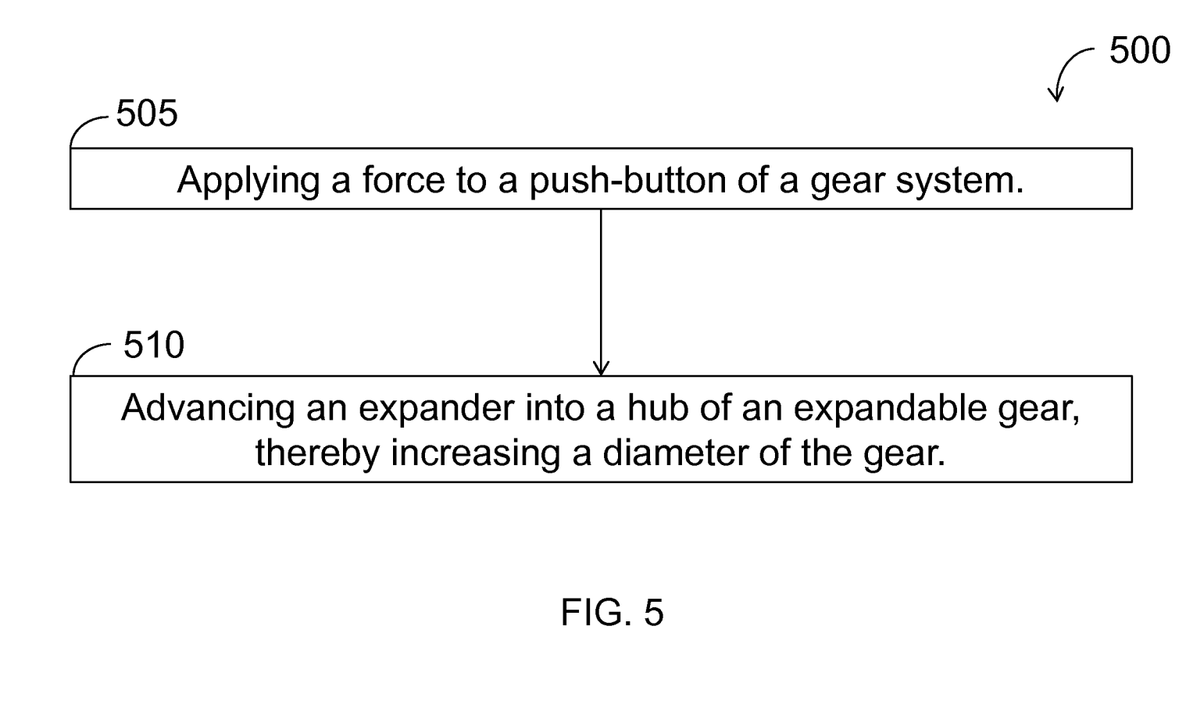
FIG. 5 is an example flow chart of a method according to one example embodiment.

In a second aspect, the invention provides a method 500 for resizing the gear system 100 according to the first aspect of the invention. The method includes, at block 505, applying a force to a push-button of a gear system and then, at block 10, advancing an expander into a hub of an expandable gear, thereby increasing a diameter of the gear.

In one embodiment, the method 500 may further include repositioning an axle of a stabilizing gear in a channel of a housing in response to the gear expanding. This beneficially permits an adequate amount tension to remain in the drive belt so the gear system will continue to operate.

In another embodiment, the method 500 may further include pivoting a lever arm coupled to a guide stem of an expander in response to the application of force to the push-button and pulling the expander into the hub via the lever arm.

In a further embodiment, the method 500 may also include packing a stent graft into a lumen such that the length of the deployed stent ranges from about 0% to about 20% shorter than the original unconstrained length. In one embodiment, a distance of travel ("T") of the push button from the unexpanded position to the expanded position to achieve a desired degree stent packing may be determined based up on the following relationship:

$$T = r * (\Delta L) * \tan \Theta^{-1}.$$

Here, "r" is the radius of the expandable gear in the unexpanded position, "ΔL" is the difference in length between an unconstrained length of the stent graft prior to deployment and the desired length of the stent graft deployed in vivo and "Θ" is the acute angle of the outer surface of the expander relative to a longitudinal axis of the expander.

The above detailed description describes various features and functions of the disclosed expandable gear and pulley systems and methods of use with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A gear system, comprising:
    an expandable gear that defines a plurality of circular sectors having a wedge-shape, wherein the plurality of circular sectors are adjoined thereby forming a contiguous perimeter in the unexpanded position;
    a hub disposed in the gear, wherein the hub comprises an expandable portion; and
    an expander, wherein the expandable gear has an expanded position when the expander is disposed within the hub and the expandable gear has an unexpanded position when the expander is disposed outside of the hub.

2. The gear system of claim 1, further comprising an expandable band disposed about a circumference of the expandable gear.

3. The gear system of claim 2, wherein the band defines at least one groove on an outer surface.

4. The gear system of claim 1, wherein the plurality of circular sectors of the expandable gear is three circular sectors each having a central angle of about 120 degrees.

5. The gear system of claim 1, wherein the plurality of circular sectors of the expandable gear is four circular sectors each having a central angle of about 90 degrees.

6. The gear system of claim 1, wherein the plurality of circular sectors of the expandable gear are displaced by the expander in a direction away from a center of the expandable gear in the expanded position.

7. The gear system of claim 1, wherein the expandable portion of the hub comprises a plurality of limbs.

8. The gear system of claim 1, wherein the expandable portion of the hub has a cross-section defining a plurality of circular sectors in the unexpanded position.

9. The gear system of claim 1, wherein the hub comprises an axle having a first end and a second end, wherein the first end of the axle is coupled to the expandable gear, wherein the expandable portion of the hub is defined at the first end of the axle and extends along the axle towards the second end of the axle.

10. The gear system of claim 1, wherein the hub comprises a coupling having a first end and a second end, wherein the first end of the coupling is attached to a non-expandable portion of the hub, wherein the second end of the coupling is configured to attach to an axle.

11. The gear system of claim 1, wherein the hub defines an opening in the unexpanded position.

12. The gear system of claim 1, wherein the expander has a tapered outer surface.

13. The gear system of claim 1, wherein the expander has a cone shape or a frustum shape.

14. The gear system of claim 1, wherein the expander comprises a guide stem at least partially disposed in the opening of the hub.

15. The gear system of claim 14, wherein the guide stem is configured to extend into and advance along a channel defined in by expandable portion of the hub.

16. The gear system of claim 14, wherein the expandable portion of the hub is coupled to an axle having a hollow core and wherein the guide stem extends through the expandable portion of the hub and through the hollow core of the axle in both the expanded and unexpanded positions.

17. The gear system of claim 14, further comprising a first push-button coupled to the expander and arranged on a surface of the expander opposite to the guide stem.

18. The gear system of claim 14, further comprising a lever arm having a first end and a second end, wherein the first end of the lever arm is coupled to the guide stem and the second end of the lever arm is coupled to a push-button.

19. The gear system of claim 17, further comprising a housing, wherein a portion of the first push-button is disposed through a first opening in the housing.

20. The gear system of claim 18, wherein a portion of the push-button is disposed through an opening in a housing, and wherein the lever arm is pivotally coupled to the housing at a point between the first and the second end of the lever arm.

21. The gear system of claim 1, further comprising a belt in mechanical communication with the expandable gear.

22. The gear system of claim 21, further comprising a stabilizing gear in mechanical communication with the expandable gear via the belt.

23. The gear system of claim 22, wherein an axle is coupled to the stabilizing gear, wherein the axle of the stabilizing gear is moveably disposed in a channel defined in a gear support such that the axle of the stabilizing gear may be repositioned within the channel.

24. The gear system of claim 23, wherein a spring is in mechanical communication with the axle of the stabilizing gear.

25. The gear system of claim 2, wherein a groove is defined along the circumference of the expandable gear, and wherein the expandable band includes a rib sized and shaped to mate with the groove of the expandable gear.

26. The gear system of claim 1, wherein the expandable gear is coupled to one of a push reel or a pull reel.

27. The gear system of claim 19, further comprising a recoil material coupled between the housing and the expander such that the expander is biased toward the unexpanded position.

28. A method for resizing a gear system, the method comprising:
    applying a force to a push-button of a gear system according to claim 1; and
    advancing an expander into a hub of an expandable gear, thereby increasing a diameter of the gear.

29. The method of claim 28, further comprising:
    repositioning an axle of a stabilizing gear in a channel of a housing in response to the gear expanding.

30. The method of claim 28, further comprising:
    pivoting a lever arm coupled to a guide stem of an expander in response to the application of force to the push-button; and
    pulling the expander into the hub via the lever arm.

31. The method of claim 28, further comprising:
    packing a stent graft into a lumen such that the length of the deployed stent ranges from about 0% to about 20% shorter than the original unconstrained length.

32. The method of claim 28, wherein a distance of travel ("T") of the push button from the unexpanded position to the expanded position is determined by:

$$T = r * (\Delta L) * \text{Tan } \theta^{-1}.$$

* * * * *